United States Patent [19]

Holland

[11] 4,329,356

[45] May 11, 1982

[54] TREATMENT OF HYPERTENSION WITH FLUOXETINE AND L-5-HYDROXYTRYPTOPHANE

[75] Inventor: Donald R. Holland, Indianapolis, Ind.

[73] Assignee: Eli Lilly and Company, Indianapolis, Ind.

[21] Appl. No.: 202,847

[22] Filed: Oct. 31, 1980

[51] Int. Cl.$^3$ .................. A61K 31/40; A61K 31/135; A61K 31/195; A61K 31/24; A61K 31/15

[52] U.S. Cl. .................. 424/274; 424/309; 424/319; 424/327; 424/330

[58] Field of Search .............. 424/274, 309, 319, 327, 424/330

[56] References Cited

U.S. PATENT DOCUMENTS

| | | | |
|---|---|---|---|
| 4,018,895 | 4/1977 | Molloy | 424/330 |
| 4,035,511 | 7/1977 | Messing | 424/330 |
| 4,194,009 | 3/1980 | Molloy | 424/330 |

OTHER PUBLICATIONS

Fuller, Res. Comm. in Chem. Path. & Pharm., vol. 10, No. 1, Jan. 1975, pp. 193–196.
Fuller, Life Sci., vol. 25, 1979, pp. 1237–1242.
Antonaccio et al., J. Pharm. Pharmac., vol. 25, 1973, pp. 495–497.
Henning et al., Acta Pharmacol. et Toxicol., vol. 29, 1971, pp. 145–154.
Krulich, Life Sci., vol. 17, 1975, pp. 1141–1144.
Fuller et al., Fed. Proc., vol. 36, No. 8, Jul. 1977, pp. 2154–2158.

*Primary Examiner*—Anna P. Fagelson
*Attorney, Agent, or Firm*—James L. Rowe; Arthur R. Whale

[57] ABSTRACT

Fluoxetine alone or a combination of fluoxetine and l-5-hydroxytryptophan, preferably also with a peripheral decarboxylase inhibitor, is administered to hypertensive mammals to lower blood pressure.

16 Claims, No Drawings

TREATMENT OF HYPERTENSION WITH FLUOXETINE AND L-5-HYDROXYTRYPTOPHANE

BACKGROUND OF THE INVENTION

Fluoxetine—N-methyl 3-(p-trifluoromethylphenoxy)-3-phenylpropylamine—is described in U.S. Pat. No. 4,018,895, which patent claims a method of treating humans suffering from depression. Pharmaceutical formulations containing fluoxetine are disclosed and claimed in U.S. Pat. No. 4,194,009. The chief pharmacological activity of fluoxetine is as a specific inhibitor of the serotonin neuron pump; i.e., as a serotonin uptake inhibitor. Administration of fluoxetine thus decreases serotonin turnover and release in mammals. In addition, there is a decrease in the output of serotonin neurons. These serotonin neurons have been postulated as being involved in brain functions such as behavior, sleep, sexual activity and hypothalamic control of pituitary hormone release. Inhibition of serotonin uptake as by fluoxetine should enhance processes that are controlled by serotonin neurons. It is reported that fluoxetine pretreatment potentiates the depression of food-reinforced learned behavior by l-tryptophan in pigeons. Fluoxetine is said to promote morphine analgesia according to U.S. Pat. No. 4,035,511.

l-5-Hydroxytryptophan has been reported to cause a fall in blood pressure in conscious rats, in anesthetized dogs pretreated with a monoamine oxidase inhibitor, and in anesthetized cats with or without inhibition of monoamine oxidase or of peripheral decarboxylase. The compound is also said to lower blood pressure on injection directly into the cerebrospinal fluid in dogs. In cats, intracerebral ventrical injection of the same compound lowers blood pressure. The hypotensive effects of l-5-hydroxytryptophan in dogs pretreated with a monoamine oxidase inhibitor are said to be abolished or attenuated by administration of a serotonin antagonist.

Carbidopa and benserazide are used to prevent peripheral decarboxylation of l-dopa in treatment of Parkinsonism.

SUMMARY OF THE INVENTION

This invention provides a method for the lowering of blood pressure in hypertensive mammals comprising the more or less simultaneous co-administration of l-5-hydroxytryptophan and of fluoxetine.

The use of the l-5-hydroxytryptophan-fluoxetine combination in reducing systolic blood pressure in spontaneously hypertensive rats is illustrated by the following experiment in which both fluoxetine and l-5-hydroxytryptophan were injected subcutaneously at a rate of 10 mg. per kg. both singly and together simultaneously to groups of six rats each.

The following protocol was used. Male spontaneously hypertensive rats were acclimated for a period of about three months. At the time of the experiment, the rats were seven to eights months of age and weighed 380–430 g. Systolic blood pressure was determined indirectly at 25° C. with an automated, 24-rat system using photoelectric sensors. On the day of the experiment, rats were transferred to individual holders and before-treatment blood pressure determined at least 30 minutes thereafter to minimize stress from handling. Rats were kept in their holders throughout the experiment. Multiple measurements were made on each rat at each time period. Heart rates were also observed.

Table 1, which follows, gives the results of this experiment. In the table, column 1 gives the time in hours after injection of the drug or drugs when the systolic blood pressure was measured; column 2, the mean blood pressure in millimeters of mercury for the group of rats given fluoxetine alone; column 3, the same information for a group of rats given l-5-hydroxytryptophan alone; column 4, the same information for a group of rats given both fluoxetine and l-5-hydroxytryptophan; and column 5, the mean systolic blood pressure for a group of rats administered only the injection vehicle. In the table an asterisk indicates that the change in systolic blood pressure from zero time is significantly different from the change observed in the control group and a cross indicates that the change from the mean systolic blood pressure at zero time is significantly different from the change observed in the fluoxetine—l-5-hydroxytryptophan group (column 4). In the table, all comparisons are made using Duncan's multiple range test ($P=0.05$).

TABLE 1

Antihypertensive effect of fluxetine and l-5-hydroxytryptophan in spontaneously hypertensive rats Systolic blood pressure (mm Hg), mean ± s.e.m.

| timer, hours | Fluoxetine | l-5-Hydroxy Tryptophan | Fluoxetine + l-5-Hydroxy Tryptophan | Vehicle (Control) |
|---|---|---|---|---|
| 0 | 193 ± 6 | 186 ± 3 | 197 ± 8 | 201 ± 8 |
| 1 | 170 ± 8 | 163 ± 3 | 149 ± 13* | 192 ± 10 |
| 3 | 167 ± 14 | 173 ± 5+ | 138 ± 10* | 188 ± 8 |
| 4 | 160 ± 9 | 161 ± 3 | 150 ± 9* | 188 ± 5 |
| 5 | 153 ± 10 | 164 ± 3+ | 141 ± 8* | 173 ± 5 |

*The change from the pre-drug value is significantly different from the change observed in the vehicle group.
+The change from the pre-drug value is significantly different from the change observed in the fluoxetine + 5-HTP group.

The combination of fluoxetine and l-5-hydroxytryptophan also produced a distinct antihypertensive effect in DOCA hypertensive rats. In this study, male Sprague-Dawley rats weighing 200–320 g. were made hypertensive by subcutaneous injection of deoxycorticosterone acetate at a rate of 10 mg. per rat per day five days per week for a three week period. An aortic cannula was placed in the aorta of each animal 24 hours before the test. All drugs were administered intraperitoneally. Both systolic and diastolic blood pressures were measured using a Statham p23Db pressure transducer and a Grass Model 7 polygraph. Heart rate was also monitored.

Table 2, which follows, gives the results of this experiment. The various columns correspond to those in Table 1. In the table, an asterisk indicates that the change from the pre-drug value is significantly different from the change observed in the vehicle group and a cross indicates that the change in the pre-drug value is significantly different from the change observed with fluoxetine plus l-5-hydroxytryptophan.

TABLE 2

Antihypertensive effect of fluoxetine and l-5-hydroxytryptophan in DOCA hypertensive rats Systolic blood pressure (mm Hg), mean ± s.e.m.

| Time, hours | Fluoxetine | l-5-Hydroxy Tryptophan | Fluoxetine + l-5-Hydroxy Tryptophan | Vehicle (Control) |
|---|---|---|---|---|
| 0 | 211 ± 9 | 214 ± 7 | 210 ± 6 | 215 ± 10 |
| 1 | 196 ± 10*+ | 204 ± 7+ | 173 ± 6* | 213 ± 8 |

TABLE 2-continued

Antihypertensive effect of fluoxetine and
l-5-hydroxytryptophan in DOCA hypertensive rats Systolic blood pressure (mm Hg), mean ± s.e.m.

| Time, hours | Fluoxetine | l-5-Hydroxy Tryptophan | Fluoxetine + l-5-Hydroxy Tryptophan | Vehicle (Control) |
|---|---|---|---|---|
| 2 | 198 ± 10*+ | 210 ± 8+ | 180 ± 7* | 218 ± 9 |
| 4 | 199 ± 9* | 203 ± 7* | 188 ± 7* | 221 ± 11 |
| 24 | 221 ± 9+ | 213 ± 10 | 199 ± 6 | 216 ± 9 |

*The change from the pre-drug value is significantly different from the change observed in the vehicle group.
+The change from the pre-drug value is significantly different from the change observed in the fluoxetine + 5-HTP group.

In similar experiments with anesthetized dogs, the combination of fluoxetine and l-5-hydroxytryptophan gave significant reductions in blood pressure. In this experiment, male mongrel dogs weighing 10 to 17 kg. were anesthetized with sodium pentabarbital (35 mg./kg. iv followed by constant intravenous infusion at 0.75 mg./kg./min.). Blood pressure was measured through a heparin-filled cannula in the left femoral artery using a Statham p23Db pressure transducer and a Beckman strip chart recorder. Mean pressure was obtained from the signal averaging mode of the recorder. Heart rate was also monitored. Five groups of dogs were employed. Table 3, which follows, gives the results of these experiments. In the table, column 1 gives the elapsed time after drug injection for blood pressure measurement; column 2, the drug employed; and columns 3–7 the mean systolic blood pressures in millimeters of mercury. Beneath each of the lower figures in parenthesis is given the change in pressure plus or minus a standard error calculated from pre-drug values. Student's "t" test was used to compare changes in groups 3, 4 or 5 from those observed in control group 1. The group 1 dogs received only l-5-hydroxytryptophan at a 3 mg./kg. dose iv. The group 2 dogs received only fluoxetine at a 5 mg./kg. dose iv. The group 3 dogs received fluoxetine at a 1 mg./kg. dose iv followed 70 minutes later by l-5-hydroxytryptophan at a 3 mg./kg. dose iv. The group 4 and 5 dogs had the same dose of l-5-hydroxytryptophan 70 minutes after injection of fluoxetine, but the fluoxetine doses were, respectively 2.5 mg./kg. in group 4, and 5 mg./kg. in group 5. The number of dogs were as follows; group 1, 6; group 2, 5; group 3, 4; group 4, 6; and group 5, 6.

In the above demonstrations of hypotensive activity utilizing the drug combination of this invention, the drugs were administered parenterally. In actual use, however, to lower the blood pressure of mammals, and in particular of humans, the oral route of administration would be preferred. In administering fluoxetine by either route, a pharmaceutically-acceptable salt formed with a non-toxic acid is employed.

Useful non-toxic acids for such purpose include inorganic acids such as: hydrochloric acid, phosphoric acid, sulfuric acid, hydrobromic acid, hydriodic acid, phosphorus acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptaonate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

For administration by either the parenteral or oral route, fluoxetine, in the form of a pharmaceutically-acceptable acid addition salt, is mixed with a pharma-

TABLE 3

| Elapsed Time (min) | Drug | Group 1 | Group 2 | Group 3 | Group 4 | Group 5 |
|---|---|---|---|---|---|---|
| −5 | Pre-Drug | 121 ± 7 | 116 ± 6 | 120 ± 5 | 126 ± 4 | 121 ± 8 |
| 0 | Fluoxetine | 122 ± 6 | 115 ± 7 | 121 ± 7 | 124 ± 5 | 125 ± 10 |
|  |  | (1 ± 1) | (−1 ± 5) | (1 ± 2) | (−2 ± 2) | (4 ± 3) |
| 70 | Prior to l-5-Hydroxytryptophan | 119 ± 6 | 125 ± 6 | 123 ± 4 | 128 ± 5 | 128 ± 10 |
|  |  | (−2 ± 2) | (9 ± 1) | (3 ± 2) | (2 ± 1) | (7 ± 5) |
| 75 | After l-5-Hydroxytryptophan | 116 ± 6 | 125 ± 5 | 114 ± 4 | 105 ± 10 | 104 ± 14 |
|  |  | (−4 ± 2) | (8 ± 1) | (6 ± 3) | (−21 ± 7)[b] | (−17 ± 13) |
| 80 |  | 121 ± 6 | 123 ± 5 | 111 ± 6 | 86 ± 8 | 80 ± 12 |
|  |  | (0 ± 3) | (7 ± 1) | (−8 ± 9) | (−40 ± 5)[d] | (−42 ± 12)[c] |
| 85 |  | 122 ± 7 | 123 ± 4 | 112 ± 9 | 78 ± 6 | 68 ± 10 |
|  |  | (1 ± 3) | (7 ± 1) | (−8 ± 10) | (−48 ± 3)[d] | (−54 ± 10)[d] |
| 90 |  | 122 ± 8 | 120 ± 4 | 111 ± 10 | 76 ± 6 | 63 ± 9 |
|  |  | (1 ± 3) | (4 ± 3) | (−8 ± 11) | (−50 ± 3)[d] | (−58 ± 9)[d] |
| 105 |  | 122 ± 6 | 123 ± 4 | 117 ± 9 | 82 ± 7 | 66 ± 12 |
|  |  | (1 ± 3) | (7 ± 2) | (−3 ± 9) | (−44 ± 8)[d] | (−56 ± 9) |
| 135 |  | 123 ± 7 | 122 ± 4 | 119 ± 9 | 98 ± 10 | 75 ± 11 |
|  |  | (2 ± 3) | (6 + 3) | (−1 ± 10) | (−28 ± 7) | (−46 ± 9)[d] |
| 195 |  | 120 ± 4 | 121 ± 2 | 114 ± 8 | 111 ± 8 | 89 ± 11 |
|  |  | (−1 ± 5) | (5 ± 4) | (−6 ±10) | (15 ± 4)[b] | (−32 ± 9)[b] |

[a]Values for mean blood pressure (±S.E.M.) are given in mm Hg. Changes in pressure (±S.E.M.) given in parentheses, were calculated from pre-drug values. Student's t test was used to compare changes in groups III, IV or V with changes observed in control group I.
[b]Significant difference ($p < 0.05$).
[c]Significant difference ($p < 0.01$).
[d]Significant difference ($p < 0.001$).

ceutically suitable carrier or diluent. With parenteral administration, the intravenous, subcutaneous or intraperitoneal route may be employed. Ordinarily, an isotonic solution of a fluoxetine salt is used. For oral administration, a predetermined quantity of a salt of fluoxetine with a pharmaceutically-acceptable acid, preferably a hydrochloride salt, is mixed with starch or other inert, pharmaceutically-acceptable excipient. The mixture is placed in telescoping gelatin capsules such that each capsule contains from 40-100 mg. of the fluoxetine salt. Similarly, fluoxetine hydrochloride or other salt can be mixed with starch, a binder and a lubricant and the mixture compressed into tablets each containing from 40-100 mg. of salt. The tablets may be scored if lowered or divided dosages are to be used.

l-5-Hydroxytryptophan is also administered in the form of a pharmaceutically-acceptable salt, preferably a hydrochloride. The same types of salts may be employed with l-5-hydroxytryptophan as are specified above for fluoxetine. On the other hand, l-5-hydroxytryptophan can also be administered in the form of an anionic salt with a non-toxic metal or metalloid ion; for example, a sodium or potassium salt, an ammonium salt, etc. could be employed. Since, in parenteral formulations, an isotonic solution is to be employed, it does not matter whether a cationic or anionic salt of l-5-hydroxytryptophan is employed since the ultimate species will be the same, depending only on the pH of the isotonic solution. It is also recognized that amino acids such as l-5-hydroxytryptophan can exist as zwitterions. In oral medicaments, we prefer to use an acid addition salt of l-5-hydroxytryptophan.

Although l-5-hydroxytryptophan has been specified, it is apparent that the compound could be administered as a component of a racemate, dl-5-hydroxytryptophan.

In a further aspect of this invention, administration of the combination of fluoxetine and l-5-hydroxytroptophan to humans is accompanied by administration of a peripheral decarboxylase inhibitor such as carbidopa[α-hydrazino-α-methyl-β-(3,4-dihydroxyphenyl)propionic acid monohydrate] or benserazide [N-(dl-seryl)-N''-(2,3,4-trihydroxybenzyl)hydrazine]. It is the function of these peripheral decarboxylase inhibitors to prevent the decarboxylation of l-5-hydroxytryptophan peripherally to yield serotonin. The coadministration of the peripheral decarboxylase inhibitor with l-5-hydroxytryptophan tends to prevent side effects attributable to serotonin (l-5-hydroxytryptamine) but not the central effects since the decarboxylase inhibitor will not penetrate the blood-brain barrier.

Each of the ingredients of our novel treatment process is administered individually. The daily dosage level for fluoxetine is from 40-100 mg. per day for a human. The dosage can be administered singly or in divided dosages 2, 3 or 4 times a day. The quantity of l-5-hydroxytryptophan to be administered varies from 200-1000 mg. per day per human and customarily is administered in divided dosages; thus the daily amount of amino acid is divided by the number of daily dosages to arrive at an individual dosage. Among the peripheral decarboxylase inhibitors, I prefer to employ carbidopa. It is administered at a rate of 100-300 mg. per day per human, preferably at about 200 mg. per day in dosages divided in the same way as the dosage of l-5-hydroxytryptophan is divided. Typical dosage regimens would be 35 mg. fluoxetine hydrochlorides, 350 mg. l-5-hydroxytryptophan as the hydrochloride salt, and 100 mg. of carbidopa, twice a day. In our novel treatment method, however, it is not necessary to precisely parallel the fluxoetine administration on the one hand with the l-5-hydroxytryptophan-carbidopa combination on the other. In other words, fluoxetine can be administered once a day wherease the tryptophan-inhibitor combination must be administered in divided dosages at least twice a day. Alternatively, the l-5-hydroxytryptophan-carbidopa combination can be given four times a day and the fluoxetine once or twice a day.

The daily dose levels in mg/kg of fluoxetine are 0.5-2, of l-5-tryptophan, 2-40 and of carbidopa, 1-6.

In a still further aspect of this invention, a method is provided for lowering blood pressure in hypertensive mammals by the administration of fluoxetine. The daily dosage of fluoxetine according to this aspect of my invention is the same as set forth previously; i.e., 0.5-2 mg./kg. of mammalian weight either as a single dose or in divided doses. Preferably, one of the standard pharmaceutically acceptably acid addition salts of fluoxetine is used to administer fluoxetine, and again preferably, the fluoxetine salt will be administered orally as a capsule or tablet. As can be seen from Table 2, administration of fluoxetine alone to DOCA hypertensive rats (Column 2) gives a statistically significant antihypertensive effect over a four hour period. Continued administration of fluoxetine 1-4 times a day not only maintains the initial antihypertensive effect but also incrementally increases that effect.

I claim:

1. A method for lowering blood pressure in a hypertensive mammal in need of treatment which comprises the co-administration of hypotensively effective amounts of fluoxetine and l-5-hydroxytryptophane or pharmaceutically acceptable salts thereof, the amount of said combination administered being significantly effective to reduce the blood pressure of said hypertensive mammal, compared to each alone.

2. A process according to claim 1 in which the drugs are administered orally.

3. A process according to claim 2 in which fluoxetine is administered as a hydrochloride salt.

4. A process according to claim 3 in which the fluoxetine hydrochloride daily dosage level is 0.5-2 mg./kg. of mammalian body weight.

5. A process according to claim 2 in which the l-5-tryptophane daily dose level is from 3-40 mg/kg of mammalian body weight.

6. A method for lowering blood pressure in hypertensive mammals in need of treatment which comprises the co-administration of hypotensively-effective amounts of fluoxetine, and l-5-tryptophan or pharmaceutically acceptable salts thereof, the amount of said combination, compared to each alone, being significantly effective to reduce the blood pressure of said hypertensive mammals plus a peripheral decarboxylase inhibitor in an amount sufficient to prevent side effects attributable to serotonin.

7. A process according to claim 6 in which the drugs are administered orally.

8. A process according to claim 7 in which fluoxetine is administered as a hydrochloride salt.

9. A process according to claim 6 in which the peripheral decarboxylase inhibitor is carbidopa.

10. A process according to claim 8 in which the fluoxetine hydrochloride daily dose level is from 0.5-2.0 mg/kg of mammalian body weight.

11. A process according to claim 7 in which the l-5-tryptophan daily dose level is from 2–40 mg/kg of mammalian body weight.

12. A process according to claim 9 in which the daily carbidopa dose level if from 1–6 mg/kg of mammalian body weight.

13. A method for lowering blood pressure in hypertensive mammals in need of treatment which comprises the administration to such a mammal of an antihypertensive amount of fluoxetine or a pharmaceutically-acceptable salt thereof.

14. A process according to claim 13 in which fluoxetine or a pharmaceutically-acceptable salt thereof is administered by the oral route.

15. A process according to claim 13 in which fluoxetine hydrochloride is administered.

16. A process according to claim 13 in which the fluoxetine daily dose level is from 0.5–2.0 mg/kg of mammalian body weight.

* * * * *